(12) United States Patent
Niewiadomski

(10) Patent No.: US 9,492,251 B2
(45) Date of Patent: Nov. 15, 2016

(54) BLANK WITH CODING FOR THE PRODUCTION OF TOOTH-TECHNICAL SHAPED PARTS AND PROCEDURES FOR THE IDENTIFICATION OF A BLANK

(75) Inventor: Klaus Niewiadomski, Lorsch (DE)

(73) Assignee: Sirona Dental Systems GmbH, Bensheim (DE)

(*) Notice: Subject to any disclaimer, the term of this patent is extended or adjusted under 35 U.S.C. 154(b) by 267 days.

(21) Appl. No.: 12/730,822

(22) Filed: Mar. 24, 2010

(65) Prior Publication Data
US 2011/0229857 A1   Sep. 22, 2011

(30) Foreign Application Priority Data
Mar. 16, 2010 (DE) .................. 10 2010 002 916

(51) Int. Cl.
*A61C 13/00* (2006.01)

(52) U.S. Cl.
CPC ....... *A61C 13/0022* (2013.01); *A61C 13/0009* (2013.01)

(58) Field of Classification Search
USPC .......................... 433/201.1, 203.1, 167, 223
See application file for complete search history.

(56) References Cited

U.S. PATENT DOCUMENTS

| | | | |
|---|---|---|---|
| 4,208,795 A * | 6/1980 | Muhlemann et al. ..... | 433/203.1 |
| 7,357,887 B2 | 4/2008 | May .............................. | 264/113 |
| 8,401,690 B2 | 3/2013 | Gleditzsch et al. | |
| 2008/0057266 A1* | 3/2008 | Johnson et al. ............... | 428/116 |
| 2008/0108016 A1 | 5/2008 | Holzner et al. ............ | 433/203.1 |
| 2010/0052308 A1 | 3/2010 | Balinsky et al. ............... | 283/70 |
| 2010/0297580 A1* | 11/2010 | Niewiadomski .............. | 433/167 |

FOREIGN PATENT DOCUMENTS

| | | |
|---|---|---|
| CN | 1293552 A | 5/2001 |
| DE | 101 55 780 A1 | 5/2003 |
| DE | 10 2006 052 478 A1 | 5/2008 |
| DE | 102007018594 A1 | 10/2008 |

(Continued)

OTHER PUBLICATIONS

English-language translation of official examination report dated Nov. 23, 2010 issued in German counterpart application—2 pages.

*Primary Examiner* — Mark Ruthkosky
*Assistant Examiner* — Laura C Powers
(74) *Attorney, Agent, or Firm* — Fitzpatrick, Cella, Harper & Scinto

(57) ABSTRACT

The invention relates to a blank for the production of a dental shaped body, wherein the blank has a corpus (2) of tooth restoration material, from which the shaped part to be fabricated is carved by means of a tool (4) by removal of material. The blank has coding means (1) formed on part of the surface (6) of the blank corpus (2), which coding means (1) has at least one structure (8, 9) for identification of the blank. The coding means (1) consists of a plurality of panels (5.1) at the level of the surface (6) of the corpus (2) and a plurality of panels (5.2, 5.3) incorporating a flat structure (8, 9) at a level (h1, h2) which is distinguishable from at least the level of the surface (6) of the corpus (2).

The invention further relates to a method for identifying a blank with the aid of coding means (1).

5 Claims, 2 Drawing Sheets

(56) References Cited

FOREIGN PATENT DOCUMENTS

| | | |
|---|---|---|
| DE | 112007001726 T5 | 7/2009 |
| DE | 102008013829 A1 | 10/2009 |
| GB | 2 297 261 A | 7/1996 |
| WO | WO 99/13796 | 3/1999 |
| WO | WO 01/35854 A1 | 5/2001 |
| WO | WO 2008/128946 A1 | 10/2008 |
| WO | WO 2009/016223 A2 | 2/2009 |
| WO | WO 2009016223 A2 * | 2/2009 |
| WO | 2009121952 A1 | 10/2009 |

* cited by examiner

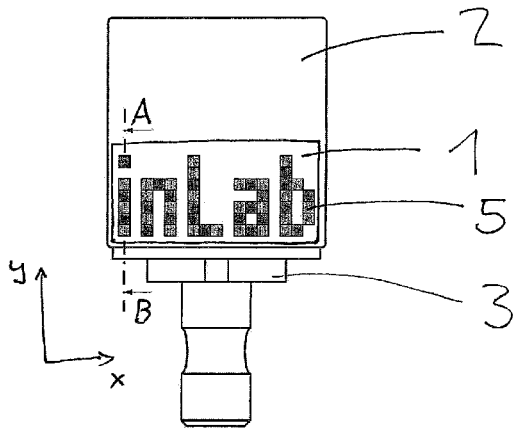
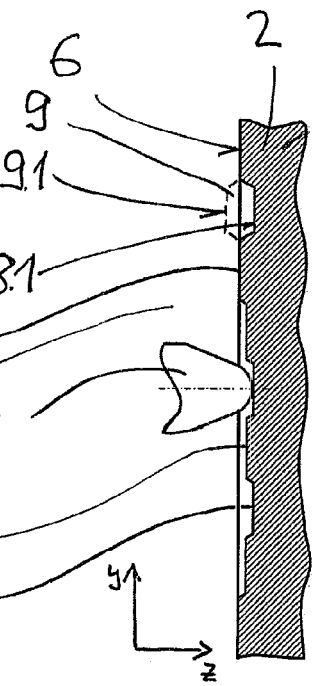
Fig. 1
Fig. 2
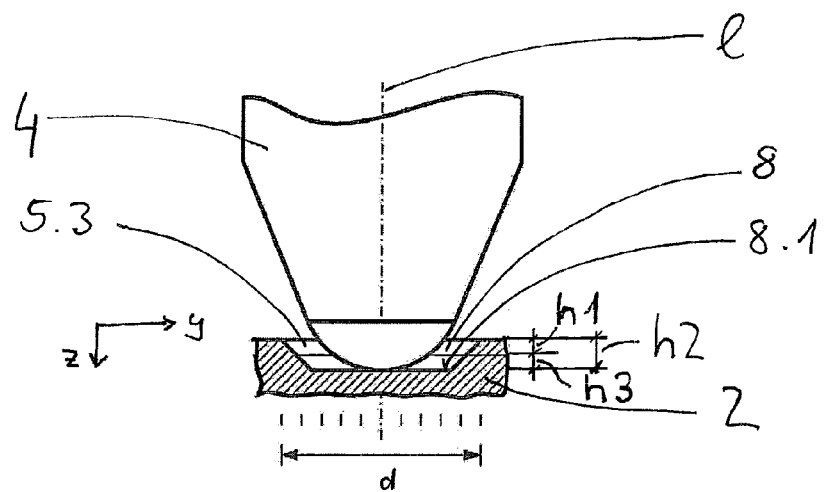
Fig. 3

BLANK WITH CODING FOR THE PRODUCTION OF TOOTH-TECHNICAL SHAPED PARTS AND PROCEDURES FOR THE IDENTIFICATION OF A BLANK

BACKGROUND OF THE INVENTION

The invention relates to a blank comprising coding means for the production of dental shaped bodies and a method for recognizing a blank by coding means.

PRIOR ART

A recognition unit is used for the identification of objects, which unit is not required for processing said objects.

Identification means involving relatively low technical elaboration is described in DE 10 2007 018 594 A1. In this case recognition of a sequence of alphanumeric characters disposed on a workpiece is carried out by means of an optical recognition unit followed by image recognition involving character recognition.

The drawbacks of such identification means are that the recognition unit is a redundant component, since it is not required for processing the workpiece. Furthermore, the identification of a blank is easy to by-pass by using a sticker made by a photocopying process and placed on the blank and does not guarantee reliable results in a dirty environment without previous cleaning.

Another means of identification is to attach an additional element to the workpiece, as described in DE 11 2007 001 726 T5. This describes an anti-fake marking process by means of a marker mounted on the product or integrated therein and an electronic memory unit and the associated method of causing the data in the memory unit to be read out by a reading device during use.

Here again, however, the reading device is a redundant component not required for processing the workpiece. Furthermore, the restriction of recognition to the machining chamber of the machine tool requires additional effort.

The possibility of effecting identification without attaching a label or an additional element to the workpiece is described in DE 101 55 780 A1. In this case, a sensor is used to scan a physical random pattern on the object fortuitously produced during the fabrication of the object to be protected or deliberately applied thereto in a non reproducible manner, for example, in the form of cords or marbling. Since the random patterns demand a relatively high resolution of the sensor, a camera is proposed as sensor. Here again, however, an additional component, namely the sensor, is necessary, which is not required for machining the workpiece. Furthermore, there is no guarantee that recognition will succeed in a dirty environment without prior cleaning. Other methods described in said patent application analyze intrinsic textures or holograms by optical means involving diffraction patterns or interferences. The sensors or analyzing processes necessary for such methods are not required for machining the workpiece and thus represent a high cost factor for the machine tool. Furthermore, recognition in a dirty environment without previous cleaning is not guaranteed.

WO 99/13796 describes a blank provided with identification coding means and a method for the production of dental restorations in which information concerning the geometry of the desired dental prosthetic item is compared with information concerning the geometries of the available blanks, in order to select that blank which is most suitable for the planned dental restoration as regards color and geometry. The coding information can be disposed on the blank, for example, in the form of a barcode or a groove or a ridge. Accordingly, this system also requires an additional device for reading the coded information.

Furthermore, WO 99/13796 describes a blank which has a recess on the corpus making it possible to achieve automatic recognition of the correct position of the blank in a machining device.

DE 10 2008 013 829 A1 describes a blank for the production of dental shaped bodies which has coding means comprising at least one structure as information carrier for properties of the blank corpus, the size or form of the structure being ascertainable by scanning or measuring the blank.

However, the structure described is one which provides information in the form of an analogous value such as the length of the blank corpus.

A blank having a structure in the form of a notch or depression on the corpus is disclosed by WO 01/35854, which notch can be implemented for aligning the blank corpus in the machine tool.

It is an object of the invention to provide a blank comprising coding means and a method for identifying the blank in which no further structural components are required.

SUMMARY OF THE INVENTION

A blank for the production of dental shaped bodies of the invention has a corpus of tooth restoration material from which the shaped part to be fabricated can be formed by means of a tool adapted to carve out material. The blank has coding means disposed on part of the surface of the blank corpus and incorporating at least one structure for identification of the blank. The coding means consists of a plurality of panels at the level of the surface of the blank corpus and of a plurality of panels having a flat structure at a level which is distinguishable from at least the level of the surface of the corpus.

The coding means has a three-dimensional design according to the invention, which design can be in the form of a word or picture, for example, so that by the associated analysis the machining tools of the machine tool themselves or calibrating means mounted in or on the toolhead of the machine tool can be implemented for recognition of the workpiece.

In particular, in the case of compressed workpieces, the characterizing features can be stored in the machine tool so that for the identification of each workpiece, that is to say of a blank of the invention, no additional components and thus no additional costs are involved.

Advantageously, at least one panel incorporating a structure is adjacent to at least one panel at the level of the surface of the corpus so that the at least one panel incorporating a structure forms a pair with the at least one panel at the level of the surface such that a difference in level is present in each pair.

On account of such a form of the coding means involving at least one panel at the level of the surface adjacent to a panel incorporating a structure, at least this panel incorporating a structure can form a pair of panels showing different levels, namely just that difference in level which exists between the structure and the adjacent surface of the two panels forming said pair. The formation of a pair of adjacent panels ensures that when the difference in level between the two panels is detected, for example by means of the tool, errors are obviated or minimized which might occur should the tool not be exactly perpendicular to the surface of the blank corpus when sensing the same.

Advantageously, the coding means may comprise at least one panel incorporating a structure showing a first difference in level relative to the surface of the blank and at least one panel incorporating a structure showing a second difference in level relative to said surface.

The provision of structures showing various differences in level relative to the surface makes it possible to generate more complex coding. In this way, the coding means shows different differences in level between different panels.

Advantageously, at least one panel incorporating a structure showing a first difference in level relative to the surface of the blank can be adjacent to a panel incorporating a structure showing a second difference in level relative to said surface, and the two panels incorporating a structure form a pair such that a difference in level is present in each such pair.

This provides greater flexibility as regards the formation of pairs or as regards the differences in level present in the coding means and suitable for being implemented for identification of the blank corpus by the coding means.

Advantageously, the structure can consist of a flat depression and/or a flat eminence relative to the surface of the blank, which depression has a base and the eminence a roof, and said base and said roof are at least approximately parallel to the surface of the blank.

Due to the structures being formed as said eminences or depressions, there is provided in the coding means an area showing a specific difference in level relative to the surface of the blank. In order to obtain a unique difference in level between a structure and the surface of the blank, it is necessary for the structure to have, as the area to be scanned, an area which is offset from, and parallel to, said surface.

Advantageously, each panel incorporating a structure can be adjacent to at least one panel at surface level. In the case of a correspondingly formed coding means, it is possible for all panels incorporating a structure to form a pair with an adjacent panel at surface level in such a manner that a difference in level is present in each pair. A corresponding coding thus makes it possible to implement all panels incorporating a structure for identification by error-optimized sensing of pairs formed in the described manner, by which means the precision of identification via the coding means is enhanced.

Advantageously, the panels incorporating a structure at least partially or completely surround a portion of the panels at surface level. In this way, the coding means can comprise not only abstract patterns but also recognizable words or pictures via an appropriate system of panels incorporating a structure arranged in lines such that they can be implemented for identification purposes.

Advantageously, each panel at surface level is adjacent to at least one panel incorporating a structure. When a picture or a word is represented within the coding means by an appropriate system of panels at surface level arranged in lines and the remaining region of the coding means filled out with panels incorporating a structure, the uniqueness of the identification of the blank corpus by the coding means is improved when as many panels at surface level as possible are, or at least can be, implemented for identification purposes. The presence of a panel incorporating a structure adjacent to each panel at surface level makes it possible to minimize errors when determining the level values.

Advantageously, the panels at surface level can at least partially and/or completely surround a portion of the panels incorporating a structure. In this way, the case previously described to the effect that a word or picture is represented by panels at surface level is made possible.

Advantageously, the coding means can comprise at least one panel which is adjacent to only panels of the same type. This is another feature that can be necessary for representing a certain word or picture within the coding means. Depending on whether a word, for example, is to be represented by lines of panels incorporating a structure or lines of panels at surface level within the coding means, it is necessary to fill all the space in between by panels of the other species. To this end it may be necessary for panels to be surrounded by panels of the same type.

Advantageously, each structure has an area of from 0.05 mm2 to 10 mm2. Thus coding means including a plurality of panels can be provided even on smaller blank corpuses to increase the precision of a coding means. It can furthermore be ensured that the structures can be sensed with a tool, in which case it is sufficient, on account of the small depth of a structure, if the diameter of the structure is greater than the diameter of the tip of the tool. The area or the diameter can therefore be less than the nominal diameter of the tool.

Advantageously, the level distinguishable from the surface of the blank corpus is in each structure not more than 500 μm. On account of this minimum depth, there is no noticeable restriction regarding the usefulness of the blank corpus. However, the depression or eminence must at least be large enough to be detected and uniquely ascertained by, say, a position measuring system present in the machine tool.

Advantageously, the corpus can be disposed in a holder and the coding means positioned at that end of the blank that is near the holder. In this way it is still possible to identify partially milled, that is to say partially used, blank corpuses by the coding means. The more regions of the coding means that are still available for identification purposes, the more precise and sure is the identification. Alternatively, residual regions on a left-over piece of block can be used for identification purposes for example when parts of the coding means have already been machined off during machining of the block.

Advantageously, the coding means can have at least five panels each incorporating a structure. An adequate number of panels and primarily of panels incorporating a structure makes it possible to include a recognizable word or picture in the coding means using panels incorporating a structure. Furthermore, a larger number of panels in all and a larger number of structures within a coding means increase the complexity and thus also the uniqueness of the coding means.

The invention also relates to a method for identifying a blank having a corpus of tooth restoration material for the production of a dental shaped body by removal of material by means of a tool held in a toolhead of a machine tool, wherein panels incorporating structures disposed in the surface of the blank are scanned by means of the tool held in the tool holder or a calibration pin held in the tool holder. Scanning of the coding means, which can consist of a plurality of panels at the level of the surface of the blank corpus and a plurality of panels incorporating a flat structure at a level that differs from at least that of the surface of the blank corpus is carried out such that at least one first panel of the coding means is scanned and, starting from the first panel, a second panel is determined from a stored assignment list of pairs of first and second panels and is likewise scanned. A difference in the levels of the two panels of the coding means is detected and from this difference in level there is obtained a pair-related reference value, which is implemented for identification purposes by comparing the reference value with a pair-related expected value. If there is conformity therewith, positive identification is assumed.

Due to the present invention, reliable recognition of a workpiece used in a CAD/CAN or CNC machine tool is possible without employing redundant components not required for machining purposes.

Due to the three-dimensional design provided by the invention for the coding means and the associated interpretation thereof, the machining tools of the machine tool themselves or alternatively calibrating means held in the tool holder of the machine tool can be implemented for recognition of the workpiece. This leads to a considerable increase in the reliability of detection in a dirty environment and to cost reduction.

Due to the present invention, a workpiece held in a machine tool is checked for the coded label "certified workpiece" by the machining tools themselves without recourse to additional components not required for machining, such as an optical recognition unit. Realization of the check-out thus involves no additional cost for the machine tool.

Sure protection from using "non-certified" workpieces can only be accomplished by checking the workpiece in the machine tool itself just prior to starting the machining operation.

In order to prevent manipulation of the workpiece during a pause in the machining process, checking can take place following a break in the machining operation, for example on account of tool fracture, as soon as machining is continued.

Optical or capacitive checking will fail in this case on account of the grinding residues or coolant residues. Not even when resorting to considerable technical expenditure on software or hardware is it possible to ensure accurate recognition without cleaning the workpiece and the recognition unit before continuing with machining.

Inductive checking requires an appropriate material property, which is not present in, for example, a ceramic block or can only be achieved by the deliberate use of special impurities or of an additional workpiece component showing inductive behavior. Here again, reliable recognition is not guaranteed without cleaning, on account of possible grinding residues.

Radiotechnical checking, for example by means of RFID, would require, in addition to the recognition unit, an additional component on the workpiece itself.

To obviate manipulation, the zone of action of the checking operation should be restricted to a small area within the machine tool.

The aforementioned sources of error are avoided by the use of mechanical checking by way of a machining tool or calibrating means in accordance with the method of the invention.

Since, for safety reasons, the machining chamber of the machine tool must always be kept closed during machining, manipulation in the recognition of the workpiece by the machining tools themselves or by calibrating means held in the toolhead is almost impossible.

Machining of non-certified, i.e. incorrectly coded, workpieces can be prevented, for example, by, allowing machining to start only after a certified workpiece has been identified.

The pairs of first and second panels of the coding means is can, for example, be stored in an assignment list on a control computer or in the machine tool itself. The latter makes it possible to carry out checking and processing of the acquired information in the machine tool itself. This makes it possible to guarantee that no impairment of the function by manipulation of the data traffic between the machine tool and a control computer is possible.

Advantageously, for each panel incorporating a structure another panel of the coding means can be stored, with which it forms a pair. By implementing all of the panels incorporating structures for forming pairs, the coding means representing, for example, a word or a picture consisting of lines formed by the panels incorporating structures, will enhance the uniqueness of the identification achieved by the method of the invention.

Advantageously, a pair consisting of a panel incorporating a structure and a panel at surface level and/or a panel incorporating a structure with a first difference in level relative to the surface of the blank and a panel incorporating a structure with a second difference in level can be formed. Identification is attained by scanning pairs of panels to detect differences in level. Differences in level greater than zero occur particularly when a structure is compared with the surface but can alternatively occur between different structures if they show different differences in level relative to the surface of the blank. Such differences in level make it difficult to falsify the coding means and therefore contribute to the uniqueness of the coding means.

Advantageously, the two panels of a pair can be adjacent to each other. When the two panels of a pair are spatially near to each other, errors in detection of the difference in level thereof are reduced which, for example, could occur on account of slightly non-perpendicular orientation of the tool relative to the surface of the blank corpus during scanning. This enhances the scanning accuracy.

Advantageously, for each panel at surface level, another panel of the coding means with which it forms a pair can be stored. If, for example, coding means are present which, for example, represent a word by way of lines of panels at surface level, and the remaining surface of the coding means consists exclusively of panels incorporating structures, the precision of the identification is increased, particularly when as many panels at surface level as possible are implemented. For this reason, the reliability of the method is increased when each panel at surface level is assigned to a pair and can thus be implemented for identification purposes.

Advantageously, at least two pairs in the coding means can be scanned. Both the reliability of identification and the duration of the method mainly depend on the number of pairs to be scanned. The more pairs that are scanned, the higher the precision of identification and the slower the procedure. In this case it is necessary to find a balance.

Advantageously, at least five pairs can be present, of which the pairs to be scanned and/or the first panel of a pair to be checked are randomly selected. If not all panels are assigned to a pair and/or if not all pairs are scanned, the random selection of the pairs and/or the first panel to be checked increases the precision of identification and thus the reliability of the method.

Advantageously, to each panel incorporating a structure there can be assigned exactly one panel at surface level, the two panels forming a pair. This ensures that each panel incorporating a structure can be queried by the present method, which enhances the precision of identification.

BRIEF DESCRIPTION OF THE DRAWINGS

The method of the invention is explained with reference to the drawings, in which:

FIG. 1 shows a blank having a corpus carrying coding means,

FIG. 2 a cross-section of the corpus shown in FIG. 1,

FIG. 3 shows a tool tip which has been brought into contact with a structure in a blank corpus.

EXEMPLARY EMBODIMENT OF THE INVENTION

FIG. 1 illustrates a blank consisting of a corpus 2 disposed in a holder 3. The corpus 2 has coding means 1, which are three-dimensionally designed and disposed at that end of the blank corpus 2 that is near to the holder such that it can be scanned and uniquely identified with the aid of the existing machining tools 4 or by means of calibrating or positioning aids, such as is illustrated in FIGS. 2 and 3.

Figure 4:
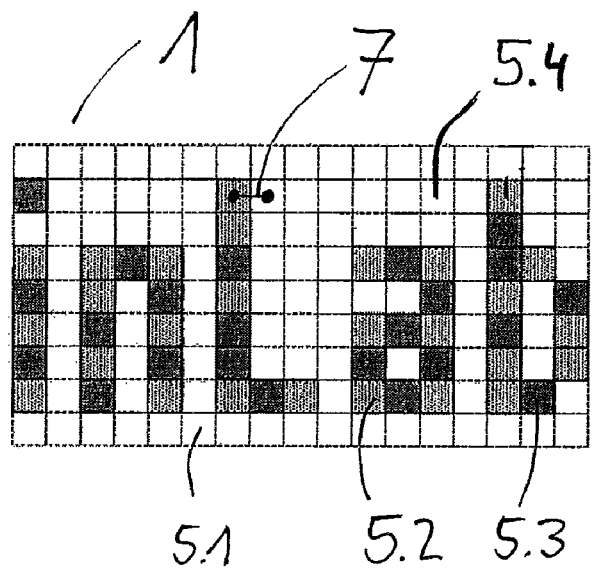
FIG. 4 shows the coding means shown in FIG. 1.

The coding means 1 is for this purpose formed according to the invention as a flat area extending in an x,y plane on the corpus 2, which coding means is divided, for example, into uniform panels 5, as outlined in FIG. 4.

FIG. 2 is a cross-section of a blank corpus 2 as shown in FIG. 1 and taken along the line AB. It can be seen that some of the panels 5.2, 5.3 are formed as structures 8, 9, for example, taking the form of depressions 8 relative to the surface 6 and having a base 8.1 below the level of the surface as regarded in the direction of the z axis. The structures 8, 9 can alternatively be in the form of eminences 9 having a raised roof 9.1 as regarded in the direction of the z axis, as indicated by dashed lines.

Some of the panels 5.1 of the coding means 1 are flush with the surface 6 of the blank corpus.

The position and shape of the panels 5 of the coding means 1 in the corpus 2, and more particularly the distribution of the structures 8, 9 within the coding means 1 are defined such that for example, a word or a picture is recognizable in the coding means 1. This is achieved, for example, in that the lines of the alphabetic characters of a word are represented by appropriately adjoining panels 5.2, 5.3 incorporating a structure 8, 9, while the spaces are completely filled by panels 5.1 at the level of the surface 6. Filling of the spaces entirely has the result that the coding means has panels 5.4 which are surrounded only by panels of the same type, as is the case in FIG. 4, for example, with some panels 5.1 being at surface level.

FIG. 3 shows a tool 4 while scanning a panel 5.3, the structure 8, 9 being in the form of a depression 8.

The structures 8, 9 are, according to the invention, geometrically designed and exhibit an appropriate diameter d such that a machining tool 4 or a calibration aid can advance toward the base 8.1 or the roof 9.1 of such a structure 8, 9 without touching the lateral delimitations of this panel or of an adjacent panel 5.

The absolute value of the depression 8 or the eminence 9 of the structure 8, 9 is such that no noticeable restriction in the usefulness of the blank corpus 2 results and the value, that is the difference in level h1, h2, of the depression 8 or the eminence 9, can still be reliably detected by the position measuring system present in the machine tool.

In the exemplary embodiment, the structures 8, 9 in the form of depressions 8 can, for example, be formed in steps of approximately 100 μm so that for example, the difference in level of a panel 5.2 incorporating the structure 8, 9 relative to the surface 2 is 100 μm and the difference in level of a panel 5.3 incorporating a structure 8, 9 is 200 μm.

The tool 4 or the calibration aid in the machine tool is positioned in the x,y plane on-center in front of a specific, arbitrary or randomly selected panel 5 of the coding means 1 in this case designed as a word and is then advanced along the longitudinal axis 1 of the tool 4 or the calibration aid, corresponding in the figures to the z axis, toward the workpiece 2.

The point of contact between the blank corpus 2 and the front, i.e. the tip, of the tool 4 or the front of the calibration aid within said panel 5 is detected either by the existing load regulation/control means for the tool 4 or the calibration aid or by some other sensor present in a regulation/control means, for example, a force sensor in the longitudinal axis 1 of the tool 4 or the calibration aid.

The position sensing means present in every CAD/CAM machine tool or CNC machine tool makes it possible to determine, as the first position, the absolute value in space of this panel 5 from the position of the tool 4 or calibration aid during detection.

The x,y position is given by the predetermined position of the tool 4 or the calibration aid in this plane. The z position is detected.

Figure 5:
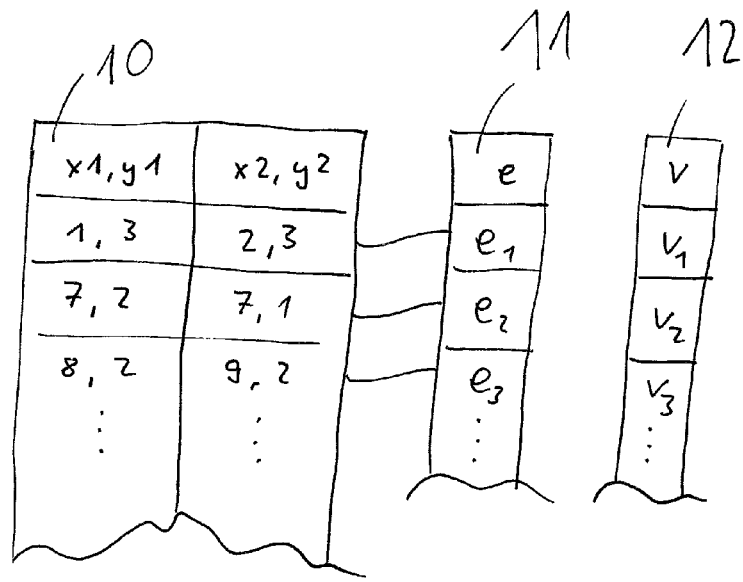
FIG. 5 shows an assignment list and stored expected values.

Starting from said first panel 5, a second panel 5 that is, a second position in the x,y plane, is determined. This is carried out with reference to an assignment list 10, as illustrated in FIG. 5, for example, in which the first panel 5 is assigned to a second panel 5, which two panels 5 form a so-called pair 7. Such a pair 7 is indicated, for example, in FIG. 4. The second panel 5 can be ascertained with reference to the assignment list 10, for example, directly in the machine tool due to storage of, inter alia, the assignment list 10 in the machine tool itself. Of course, the assignment list 10 can alternatively be stored in a control computer and the determination of the second panel 5 effected by appropriate communication between the machine tool and the control computer.

The tool 4 or the calibration aid of the machine tool is positioned in front of the second panel 5 in the x,y plane and the absolute position of this further panel 5 in space is determined in the same way as the second position.

These pairs 7 consisting of the first and second panels 5 are predetermined. The pairs 7 can, for example, always consist of a panel 5.2, 5.3 incorporating a structure 8, 9 and a panel 5.1 at the level of the surface 6 of the blank corpus 2 like the pair 7 shown in FIG. 4.

The coding means 1 can, for example, contain only panels 5 which are assigned to not more than one pair 7. Alternatively, the coding means 1 can be provided with an assignment list 10 which assigns individual panels 5 to a plurality of partner-panels, for example, to a first partner-panel with which the designated panel 5 forms a pair 7 when it is tested as the first panel 5 and to a second partner-panel with which the designated panel 5 forms a pair 7 when it is scanned as the second panel 5.

The difference in level h1, h2, h3 of the two positions defined for the two panels 5 of a pair 7 that is, the difference between the z value of the first position and the z value of the second position directly forms, for example, a reference value v, which is compared with an expected value e for the difference in level of these two panels 5 that is, of this pair 7. The result can either be used immediately for a decision concerning further machining of the workpiece 2 or be stored for evaluation following the determination of further differences. The expected values e can, for example, have been stored in a list 11 of the expected values e associated with the assignment list 10, as indicated in FIG. 5.

The provision of pairs 7 of adjacent panels 5 has the advantage that an angle error of the longitudinal axis 1 of the tool 4 or the calibration aid with respect to the x,y plane of the blank corpus 2 has only a very small influence on the determined difference in level.

The determination of further differences in level h1, h2, h3 is carried out in the same way on further pairs 7, and the selection of pairs 7 or of the first partner-panel 5 to be scanned of a pair 7 can be randomly effected. This can be carried out, for example, by the machine tool itself.

The number of determined differences in level h1, h2, h3 is governed by the number of panels 5 and by the desired degree of security against falsification. The more panels 5 that are included in a coding means 1 and the larger the proportion of scanned panels 5 compared with the unscanned panels 5 of a coding means 1, the greater is the security of the identification achieved by scanning.

The evaluation of the determined reference values v can take place, for example, only following the determination of the desired number of differences in level h1, h2, h3 and the determination of the corresponding reference values v. To this end, the determined reference values v can be stored in a list 12 of reference values v, as indicated in FIG. 5.

Execution of the method of the invention makes it possible, for example, by reason of high deviations in individual reference values v or in the sum of such values, not to start machining, and thus to prevent machining of incorrectly coded blank corpuses 2, in a machine tool carrying out the method.

LIST OF REFERENCE NUMERALS OR CHARACTERS 1 coding means
2 blank corpus
3 holder
4 tool
5 panel
5.1 panel at surface level
5.2 panel incorporating a structure showing a first difference in level relative to the surface of the blank
5.3 panel incorporating a structure showing a second difference in level relative to the surface
5.4 panel adjoining only panels of the same type
6 surface of the blank corpus
7 pair
8 depression
8.1 base of depression
9 eminence
9.1 roof of eminence
10 assignment list
11 list of expected values
12 list of the reference values
d diameter
e expected value
h1 first difference in level
h2 second difference in level
h3 difference in level
l longitudinal axis of tool
v reference value

The invention claimed is:
1. A dental blank, comprising:
a material from which a dental part is to be carved, wherein the material includes a coding region that includes:
a plurality of surface level panels, each at a surface level of the material,
a plurality of first panels, each including a first structure which is at a different level from the surface level of the material by a first amount, and
a plurality of second panels, each including a second structure which is at a different level from the surface level of the material by a second amount,
wherein a surface of the first structure extends in a plane that is approximately parallel to a plane in which a surface of the second structure extends,
wherein the surface level panels, the first panels, and the second panels are arranged to form:
(i) a first-surface panel pair comprising a first panel and a surface panel abutting the first panel,
(ii) a second-surface panel pair comprising a second panel and a surface panel abutting the second panel, and
(iii) a first-second panel pair comprising a first panel and a second panel abutting the first panel, wherein a difference in level between the first and second structures of the first and second panels that comprise the first-second panel pair is a third amount, and
wherein the surface level panels are enclosed or at least partially surrounded by the first and second panels.

2. The dental blank as defined in claim 1, wherein the first structure and the second structure are flat structures that are depressed relative to the surface of the material and are at least approximately parallel to the surface of the material.

3. The dental blank as defined in claim 1, wherein the second structure is a flat structure that is raised relative to the surface of the material and at least approximately parallel to the surface of the material.

4. The blank according to claim 1, wherein the plurality of surface panels, the plurality of first panels, and the plurality of second panels, are arranged in a two-dimensional array within the coding region.

5. A dental blank, comprising:
a material, from which a dental part can be fabricated, that includes a coding region that includes:
a plurality of surface level panels located at a surface level of the material,
a plurality of first panels, each including a first structure with a first surface located a first distance from the surface level of the material in a direction perpendicular to the surface level of the material, and
a plurality of second panels, each including a second structure with a second surface located a second distance from the surface level of the material in the direction perpendicular to the surface level of the material,
wherein the first surface extends in a plane that is approximately parallel to a plane in which the second surface extends,
wherein the plurality of surface level panels are enclosed or at least partially surrounded by the first and second panels,
wherein each of the first panels forms a first-surface panel pair with an abutting surface level panel,
wherein each of the second panels forms a second-surface panel pair with an abutting surface level panel, and
wherein abutting first and second panels form respective first-second panel pairs with a third distance between the first and second surfaces of the first and second panels, respectively.

* * * * *